(12) United States Patent
Holman

(10) Patent No.: US 7,146,205 B2
(45) Date of Patent: Dec. 5, 2006

(54) METHODS FOR DETERMINING WHETHER TO PROVIDE AN INHIBITOR OF SYMPATHETIC NERVOUS SYSTEM ACTIVITY TO A HUMAN BEING SUFFERING FROM AN AUTOIMMUNE DISEASE OR FIBRYOMYALGIA

(75) Inventor: Andrew J. Holman, Seattle, WA (US)

(73) Assignee: CNS-Rheumatology, Inc., Seattle, WA (US)

( * ) Notice: Subject to any disclaimer, the term of this patent is extended or adjusted under 35 U.S.C. 154(b) by 398 days.

(21) Appl. No.: 10/441,922

(22) Filed: May 19, 2003

(65) Prior Publication Data

US 2004/0171954 A1 Sep. 2, 2004

Related U.S. Application Data

(60) Provisional application No. 60/451,347, filed on Feb. 27, 2003.

(51) Int. Cl.
*A61B 5/04* (2006.01)

(52) U.S. Cl. .................................... 600/515
(58) Field of Classification Search ............... 600/481, 600/509–519
See application file for complete search history.

(56) References Cited

U.S. PATENT DOCUMENTS 6,482,163 B1 * 11/2002 Oka et al. ................... 600/481
2002/0045835 A1  4/2002 Masakov et al.
2004/0210261 A1 * 10/2004 King et al. ................... 607/9

OTHER PUBLICATIONS

Journal of Neurology, Neurosurgery and Psychiatry "Analysis of Heart Rate Variations in Patients with Multiple Sclerosis," B. Neubauer et al, vol. 41, pp. 417-419, 1978.*

Baevskiy, R.M., et al., *Mathematical Analysis of Changes in Heart Rate Rhythm Under Stress*, Moscow Science, 1984.

Bellavere, F., "Heart Rate Variability in Patients With Diabetes and Other Noncardiological Diseases," in Malik, M. and A.J. Camm (eds.), *Heart Rate Variability*, Futura Publishing Co., Ch. 38, pp. 507-516, 1995.

Cerutti, S., et al., "Spectral Analysis of the Heart Rate Variability Signal," in Malik, M. and A.J. Camm (eds.), *Heart Rate Variability*, Futura Publishing Co., Ch. 5, pp. 63-74, 1995.

Elenkov, I.J., et al., "The Sympathetic Nerve-An Integrative Interface Between two Supersystems: The Brain and the Immune System," *Pharmacol. Rev.* 52(4):595-638, 2000.

Hainsworth, R., "The Control and Physiological Importance of Heart Rate," in Malik, M. and A.J. Camm (eds.), *Heart Rate Variability*, Futura Publishing Co., Ch. 1, pp. 3-19, 1995.

(Continued)

*Primary Examiner*—George Manuel
(74) *Attorney, Agent, or Firm*—Christensen O'Connor Johnson Kindness PLLC

(57) ABSTRACT

The present invention provides methods for determining whether to provide an inhibitor of sympathetic nervous system activity to a human being suffering from an autoimmune disease and/or fibromyalgia. The methods of this aspect of the invention each include the steps of: (a) measuring the heart rate variability of a human being suffering from an autoimmune disease or fibromyalgia, to yield heart rate variability data; (b) analyzing the heart rate variability data to determine whether there is excessive sympathetic nervous system activity in the heart of the human being; and (c) providing an inhibitor of sympathetic nervous system activity to the human being if there is excessive sympathetic nervous system activity in the heart of the human being.

12 Claims, 6 Drawing Sheets

OTHER PUBLICATIONS

Kennedy, H.L., "Heart Rate Variability Instruments From Commercial Manufacturers," in Malik, M. and A.J. Camm (eds.), *Heart Rate Variability*, Futura Publishing Co., Ch. 10, pp. 127-132, 1995.

Kleiger, R.E., et al., "Time-Domain Measurements of Variability," in Malik, M. and A.J. Camm (eds.), *Heart Rate Variability*, Futura Publishing Co., Ch. 3, pp. 33-45, 1995.

Malik, M., "Geometrical Methods for Heart Rate Variability Assessment," in Malik, M. and A.J. Camm (eds.), *Heart Rate Variability*, Futura Publishing Co., Ch. 4, pp. 47-61, 1995.

Martínez-Lavín, M., et al., "Circadian Studies of Autonomic Nervous Balance in Patients with Fibromyalgia," *Arthritis & Rheumatism* 41(11):1966-1971, 1998.

McMillan, D.E., "Heart Rate Variability During Sleep in Fibromyalgia and Insomnia," Doctoral Dissertation, University of Washington, pp. 1-79, 2001.

Nestler, E.J., et al., "Molecular Control of *Locus coeruleus* Neurotransmission," *Biol. Psychiatry* 46:1131-1139, 1999.

Petzke, F., et al., "Sympathetic Nervous System Function in Fibromyalgia," *Current Rheumatology Reports* 2:116-123, 2000.

Raj, S.R., et al., "Dysautanomia Among Patients With fibromyalgia a Non-invasive Assessment," *Jour. of Rheumatol.*, 27(11):2660-2665, 2000.

\* cited by examiner

METHODS FOR DETERMINING WHETHER TO PROVIDE AN INHIBITOR OF SYMPATHETIC NERVOUS SYSTEM ACTIVITY TO A HUMAN BEING SUFFERING FROM AN AUTOIMMUNE DISEASE OR FIBRYOMYALGIA

CROSS-REFERENCE TO RELATED APPLICATION

This application claims the benefit of U.S. Provisional Application No. 60/451,347, filed Feb. 27, 2003.

FIELD OF THE INVENTION

The present invention relates to methods for determining whether to provide an inhibitor of sympathetic nervous system activity to a human being suffering from an autoimmune disease or fibromyalgia.

BACKGROUND OF THE INVENTION

Autoimmune diseases are diseases in which the immune system of an organism attacks some or all of the organism's own cells and/or tissues. It is known that the symptoms of an autoimmune disease may be reduced, or eliminated, in some human patients by administration of drugs that inhibit the action of one or more of the components of the immune system responsible for attacking the body's own cells or tissues. The same drug(s) may not be effective, however, to improve the symptoms of an autoimmune disease in all human patients. There is no generally accepted explanation for why some autoimmune disease patients respond favorably to drug treatment, while others do not.

In an attempt to improve the symptoms of an autoimmune disease patient who does not respond favorably to a standard dose of medication, a physician may increase the dosage, and/or administer several medications. Some patients do not respond even to an increased dosage of medication, or to a combination of medications. These patients are therefore unnecessarily subjected to extensive medication which may cause undesirable side effects.

Similarly, human patients suffering from fibromyalgia show different levels of responsiveness to drug therapy. Fibromyalgia is a common disabling disorder characterized by chronic musculoskeletal aches and pain, stiffness, general fatigue, and sleep abnormalities including diminished stage four sleep. Examination of affected patients reveals increased tenderness at muscle and tendon insertion sites, known as "tender points". Fibromyalgia patients experience severe morning stiffness and a generalized decrease in overall physical function, and they are often prone to headaches, memory and concentration problems, dizziness, numbness and tingling, and crampy abdominal or pelvic pain. Fibromyalgia affects 2–4% of the population and is most frequently found in women between 20 and 50 years old, though it can also affect men, the elderly and minors. Some human beings suffering from an autoimnune disease also suffer from fibromyalgia.

A physician can positively diagnose fibromyalgia syndrome by finding the symptoms of generalized musculoskeletal pain, and pain at more than 11 of 18 defined characteristic "tender points" when finger pressure of about 4 kg is applied to the area. The total pain score for all 18 tender points is referred to as the "tender point index" of that patient. The efficacy of a particular fibromyalgia therapy is demonstrated by observation of a statistically significant improvement in a patient's tender point index.

There is a need, therefore, to understand why some autoimmune disease patients, and patients suffering from fibromyalgia, do not respond favorably to standard medications; there is also a need for treatments that improve the symptoms of these patients; and there is a need for diagnostic tools and methods that permit identification of these patients, so that they are not unnecessarily prescribed medicines that do not improve the symptoms of their autoimmune disease, and/or fibromyalgia, and which may cause adverse side effects.

SUMMARY OF THE INVENTION

In accordance with the foregoing, the present invention is based, at least in part, on the insight that excessive sympathetic nervous system activity can contribute to the onset, and/or progression, and/or duration, and/or severity, of an autoimmune disease, and/or fibromyalgia, in a human being.

In the practice of the present invention, heart rate variability is used as a measure of sympathetic nervous system activity. Typically, lower than normal heart rate variability indicates the presence of excessive sympathetic nervous system activity. In the practice of the present invention, an inhibitor of sympathetic nervous system activity is provided to autoimmune disease patients, or fibromyalgia patients, who suffer from excessive sympathetic nervous system activity, thereby reducing or eliminating the contribution of sympathetic nervous system activity to the autoimmune disease and/or fibromyalgia. Thus, patients who are unlikely to respond to medications traditionally used to treat autoimmune disease, and/or fibromyalgia, can be identified at an early stage of their disease and more effectively treated, using an inhibitor of sympathetic nervous system activity, before the onset of debilitating disease.

Thus, in one aspect the present invention provides methods for determining whether to provide an inhibitor of sympathetic nervous system activity to a human being suffering from an autoimmune disease and/or fibromyalgia. The methods of this aspect of the invention each comprise the steps of: (a) measuring the heart rate variability of a human being suffering from an autoimmune disease or fibromyalgia, to yield heart rate variability data; (b) analyzing the heart rate variability data to determine whether there is excessive sympathetic nervous system activity in the heart of the human being; and (c) providing an inhibitor of sympathetic nervous system activity to the human being if there is excessive sympathetic nervous system activity in the heart of the human being.

Heart rate variability can be measured, for example, by measuring the temporal variation between the occurrence of the same electrocardiogram feature on a multiplicity of successive heart beats. Heart rate variability can be analyzed, for example, by using Fourier transformation analysis of the heart rate variability data. In some embodiments of the methods of the invention, steps (a) and (b) together occur within a period of less than one hour. In some embodiments, steps (a) and (b) together occur within a period of less than half an hour. In some embodiments, steps (a) and (b) together occur within a period of less than five minutes.

The methods of the invention are useful in any situation in which it is desirable to determine whether to provide an inhibitor of sympathetic nervous system activity to a human being suffering from an autoimmune disease and/or fibromyalgia. For example, some embodiments of the methods of the invention are practiced in a few minutes in a physician's office and can be used to rapidly identify human patients who suffer from an autoimmune disease and/or fibromyalgia, and who also suffer from excess sympathetic nervous system activity. These patients are provided with an inhibitor of sympathetic nervous system activity. Patients suffering from an autoimmune disease are also typically, although not necessarily, provided with a medication that inhibits the action of a component of the immune system that contributes to the autoimmune disease. Patients suffering from fibromyalgia are also typically, although not necessarily, provided with an art-recognized medication for the treatment of fibromyalgia.

Again by way of example, some embodiments of the methods of the invention are practiced in a few minutes in a physician's office and can be used to rapidly identify those autoimmune disease patients, and/or fibromyalgia patients, who do not respond to conventional medications for their disease, and who also suffer from excessive sympathetic nervous system activity. These patients are provided with an inhibitor of sympathetic nervous system activity and typically, although not necessarily, are also provided with an art-recognized medication for treating the autoimmune disease and/or fibromyalgia.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
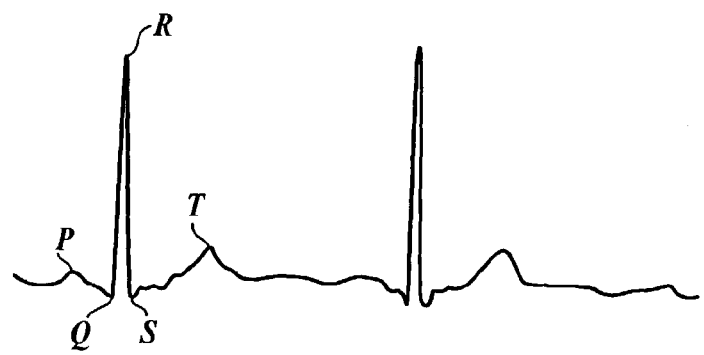
FIG. 1 shows a typical electrocardiogram of a healthy human being. The electrocardiogram includes the following features: a P wave, a Q feature, an R peak, an S feature and a T wave.

In one aspect the present invention provides methods for determining whether to provide an inhibitor of sympathetic nervous system activity to a human being suffering from an autoimmune disease and/or fibromyalgia. The methods of this aspect of the invention each comprise the steps of: (a) measuring the heart rate variability of a human being suffering from an autoimmune disease or fibromyalgia, to yield heart rate variability data; (b) analyzing the heart rate variability data to determine whether there is excessive sympathetic nervous system activity in the heart of the human being; and (c) providing an inhibitor of sympathetic nervous system activity to the human being if there is excessive sympathetic nervous system activity in the heart of the human being.

As used herein, the term "heart rate variability" refers to the variation in the temporal intervals between successive heart beats.

As used herein, the term "autoimmune disease" refers to a disease in which an organism's immune system attacks some or all of the organism's own cells and/or tissues. Representative examples of autoimmune diseases include rheumatoid arthritis; psoriatic arthritis; spondyloarthropathy; palindromic rheumatism; systemic lupus erythematosus; vasculitis with systemic lupus erythematosus; multiple sclerosis; Hashimoto's thyroiditis; chronic pseudogout; hepatitis C arthritis, mixed connective tissue disease; dermotamyositis, polymyositis; scleroderma; Sjogren's syndrome; cryoglobulinemia; Crohn's disease; ulcerative colitis; autoimmune hepatitis; sclerosing cholangitis; primary biliary cirrhosis; autoimmune pneumonitis; autoimmune cerebritis; thyroiditis; graft versus host disease; Myasthenia gravis; pemphigus vulgaris; temporal arteritis; polymyalgia rheumatica; autoimmune hemolytic anemia; idiopathic thrombocytopenic purpura; thrombotic thrombocytopenic purpura; hemolytic uremic syndrome; Sweet's syndrome; polyarteritis nodosa; microscopic polyarteritis nodosa; amyloidosis; sarcoidosis; and familial Mediterranean fever. The spondyloarthropathy can be, for example, Behcet's disease, sarcoidosis, ankylosing spondylitis, Whipple's Disease or Reiter's Syndrome.

In the practice of the methods of the invention, the heart rate variability of a human being, suffering from an autoimmune disease and/or fibromyalgia, is measured. The heart rate variability provides an indirect measurement of the level of activity of the autonomic nervous system that innervates the heart, and, when subject to appropriate analysis, the heart rate variability provides information about the levels of activity of the sympathetic and parasympathetic components of the autonomic nervous system that innervates the heart.

The human nervous system consists of two major subdivisions: the central nervous system and the peripheral nervous system. The central nervous system consists of the brain and spinal cord. This is where almost all the important processing in the nervous system takes place. The peripheral nervous system relays sensory input and motor outflow between the periphery and the central nervous system.

The autonomic nervous system is one of the two divisions of the peripheral nervous system. The autonomic nervous system regulates some glands, and also smooth and cardiac muscles. The activity of the autonomic nervous system tends to be mostly automatic and unconscious, although it can be influenced by psychological stress.

The autonomic nervous system is divided into two parts: the sympathetic nervous system and the parasympathetic nervous system. Most of the viscera receive innervation from both sympathetic and parasympathetic nerve fibers, but the effects produced by activity in the two systems generally oppose one another. Activity in the sympathetic nervous system is generally associated with an increase in the level of excitation of an organism. It is sometimes called the "fight or flight" system. The parasympathetic nervous system, on the other hand, is generally thought of as "vegetative", being concerned with the body's recovery from exertion, or active when the body is in its resting state. For example, the sympathetic nervous system stimulates an increase in heart rate, while the parasympathetic nervous system causes a decrease in heart rate.

The human heart has a natural "pacemaker" called the sinoatrial node. The sinoatrial node is a specialized group of cells at the top of the upper-right chamber (the right atrium) of the heart. Anywhere between 60 and 100 times a minute, the sinoatrial node sends an electrical impulse throughout the heart to cause it to beat (contract). When the sinoatrial node sends an electrical impulse, that impulse first travels through the upper chambers (the atria) of the heart. The impulse then passes through a small group of cells called the atrioventricular node. The atrioventricular node checks the impulse and sends it along a bundle of electrically conductive fibers, that divide into a right bundle branch and a left bundle branch, which lead to the heart's lower chambers (the ventricles).

The parasympathetic nervous system innervates the sinoatrial node, the electrically conductive fibers, and the atrial muscle. Parasympathetic stimulation rapidly slows heart rate. Sympathetic nerves innervate the entire heart, including the sinoatrial node, the electrically conductive fibers, and the atrial and ventricular heart muscle. Increased activity in the sympathetic nerves results in increases in both heart rate and the force of contraction.

The heart rate of a resting person shows some variability which is due, at least in part, to the dynamic interplay of the sympathetic and the parasympathetic nervous systems, which act in balance to maintain cardiac function. This heart rate variability can be measured by measuring the electrical activity of the autonomic nervous system in the heart. The electrical activity in the heart is typically shown as an electrocardiogram. A typical electrocardiogram trace for a healthy human being is shown in FIG. 1, and shows several recognized and well-characterized features (identified by the letters P, Q, R, S and T) of the electrical activity associated with each heart beat.

Thus, for example, the time period between successive beats (and the variation in that time period) can be measured by measuring the time interval between the same electrocardiogram feature associated with successive heart beats. For example, the time interval between two successive heart beats can be measured by measuring the time interval between the peak of the P wave on each of the successive heart beats. Again by way of example, the time interval between two successive heart beats can be measured by measuring the time interval between the R peak on each of the successive heart beats.

Heart rate variability can be determined by measuring the variation in time intervals between the same feature (e.g., R peak) in a series of successive heart beats. Typically, in the practice of the present invention, heart rate variability data is mathematically analyzed to determine whether there is excessive sympathetic nervous system activity in the heart of a human being suffering from an autoimmune disease and/or fibromyalgia. The presence of excessive sympathetic nervous system activity in the heart is typically revealed by lower than normal heart rate variability. Numerous art-recognized mathematical techniques exist for analyzing heart rate variability data, such as the mathematical techniques disclosed in M. Malik and A. J. Camm (eds.) *Heart Rate Variability*, Armonk, N.Y. Futura Publishing Company Inc, (1995), which publication is incorporated herein by reference.

For example, the arithmetic mean of the heart beat intervals over a measured time period can be calculated. Again by way of example, the standard deviation of the heart beat intervals can be calculated (e.g., the standard deviation of the R—R interval between successive heart beats measured during a defined time period).

Again by way of example, so-called time-domain measurements of heart rate variability include the root mean square successive differences where each difference is squared, summed, the result averaged, and then the square root obtained. These measurements also include the proportion or number of differences between adjacent cycles that exceed an arbitrary limit. Variables that reflect the proportion of differences include pNN50 (the proportion of cycles where the difference is greater than 50 milliseconds), and pNN6.25% (the proportion of cycles where the difference is greater than 6.25% of the mean heart period). A description of time-domain measurements of heart rate variability is set forth in Chapter 3 of M. Malik and A. J. Camm (eds.) *Heart Rate Variability*, Armonk, N.Y. Futura Publishing Company Inc, (1995).

Figure 2:
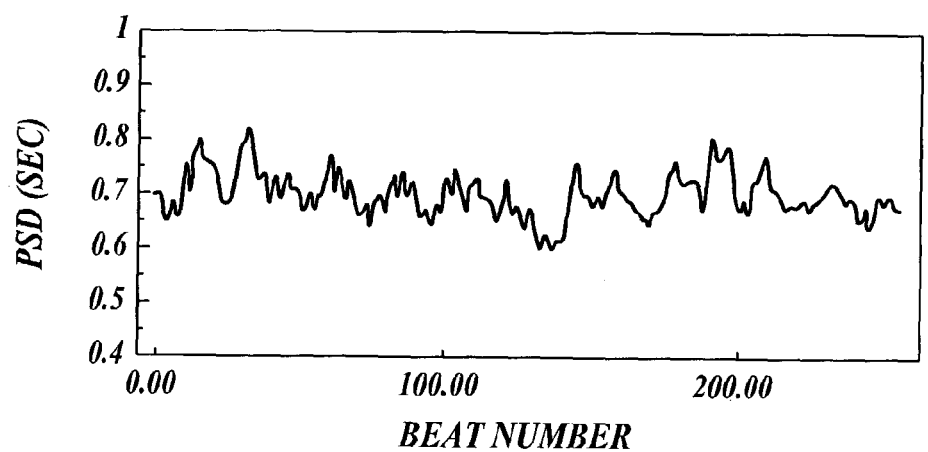
FIG. 2 shows a typical tachogram of a healthy human being.
Figure 3:
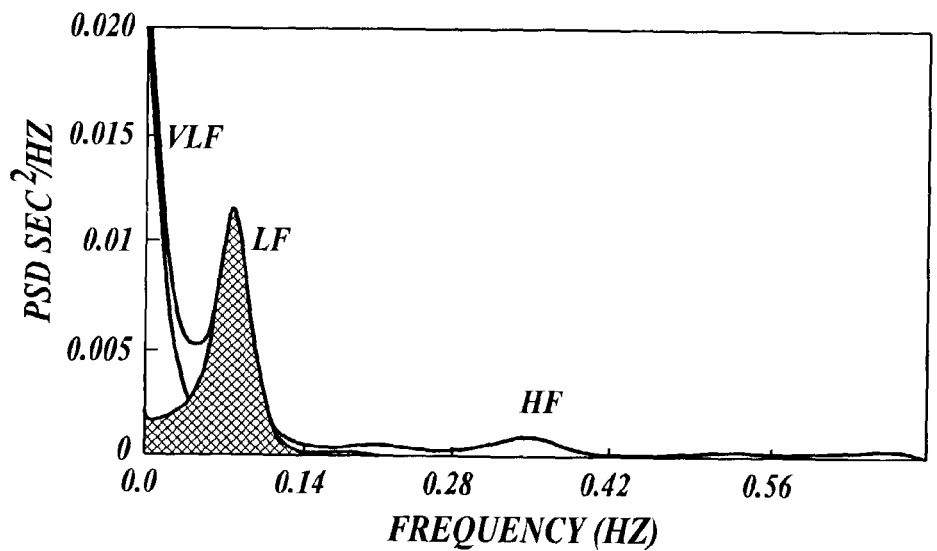
FIG. 3 shows the Power Spectral Density of the tachogram shown in FIG. 2.

For a deeper insight into the dynamics underlying the beat-to-beat variations, and for understanding how the overall variance is distributed in different frequency contributions, more advanced techniques can be applied, based on second order statistics, through the calculation of the autocorrelation function and its Fourier transform, the Power Spectral Density. In this regard, the heart rate variability electrical signal contains well-defined rhythms that can be identified from a tachogram that shows the time between successive beats plotted against the beat number. Thus, for example, FIG. 2 shows the R-peak-to-R-peak tachogram series for a normal subject in control conditions (relaxed on a bed). The Power Spectral Density of the series is shown in FIG. 3, and shows three main rhythms, that contribute to the total power, which are identifiable in three different frequency ranges.

Long period rhythms are contained in the very low frequency (VLF) range, between direct current and 0.03 Hz. These account for the long-term regulation mechanisms probably related to thermoregulation, to the renin-angiotensin system and to other humoral factors. In the low frequency (LF) range, between 0.03 and 0.15 Hz, there is a rhythm, generally centered around 0.1 Hz. Both sympathetic and parasympathetic contributions can be involved in this activity. However, an increase in its power has always been observed as a consequence of sympathetic activation. Thus, an increase in the LF power is generally accepted as a marker of sympathetic activation. At the respiratory frequency, generally in a wide range between 0.18 and 0.4 Hz, there is a high frequency (HF) component. This rhythm is mediated by the vagus nerve on the heart, and so is generally accepted as a marker of parasympathetic activation. Representative art-recognized algorithms for generating the Power Spectral Density of the heart rate variability signal are set forth in Chapter 4 of M. Malik and A. J. Camm (eds.) *Heart Rate Variability*, Armonk, N.Y. Futura Publishing Company Inc, (1995).

Figure 4:
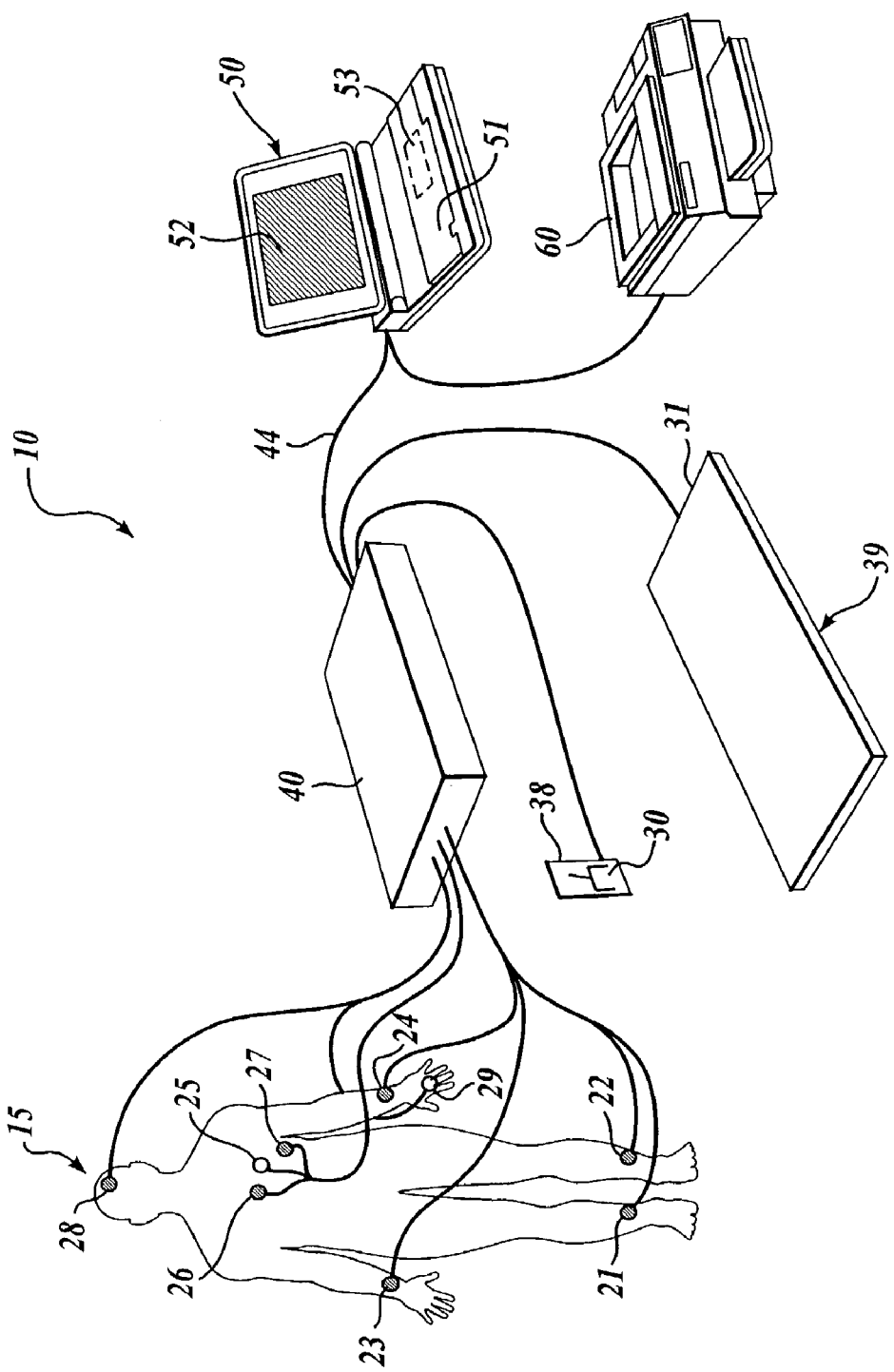
FIG. 4 shows a diagrammatic representation of a non-invasive testing system useful in the practice of the present invention.

A presently preferred system for measuring heart rate variability in the practice of the present invention is described in published United States patent application serial number U.S. 2002/0045835 A1, which is incorporated herein by reference. This system is commercially available as The OmegaWave Sport Technology System, which is sold by OmegaWave Sport, Inc., 2732 Sunnyview Lane, Eugene, Oreg. 97405, USA. In brief, FIG. 4 is a diagrammatic representation of a non-invasive diagnostic testing system 10 (The OmegaWave Sport Technology System) useful in the practice of the present invention. FIG. 4 illustrates one embodiment of components of the system and various electrode/sensor placements on the human body. System 10 is adapted to perform the following tests on a human body: Heart Rate Variability; Differential electrocardiogram (ECG); Omega Wave; Jump; and Stimulus Response. In the practice of the present invention, system 10 is used to perform the Heart Rate Variability test.

The non-invasive diagnostic system 10 includes a plurality of sensors 21–31 (sensors 30 and 31 are provided in the reaction button 38 and contact mat 39, respectively) for assessing the functional state of a person receiving a test (PRT) 15. These sensors are coupled to an interface device 40 that functions to channel signals through to a computing device 50 and to protect a person receiving a test from electrical shock. Interface device 40 (which is discussed in more detail with reference to FIG. 5) preferably amplifies, filters and digitizes analog signals from sensors 21–31.

Computing device 50 may be a conventional computer (laptop, personal or other) or another computing device (for example, that includes processing circuitry, memory, operator input control and a display element or access to same). In FIG. 4, computing device 50 is illustrated as a personal computer 50 with a keyboard 51, a monitor 52 and processing logic 53. Computing device 50 may be coupled to a printer 60 to generate, for example, a printed copy of test results.

Figure 5:
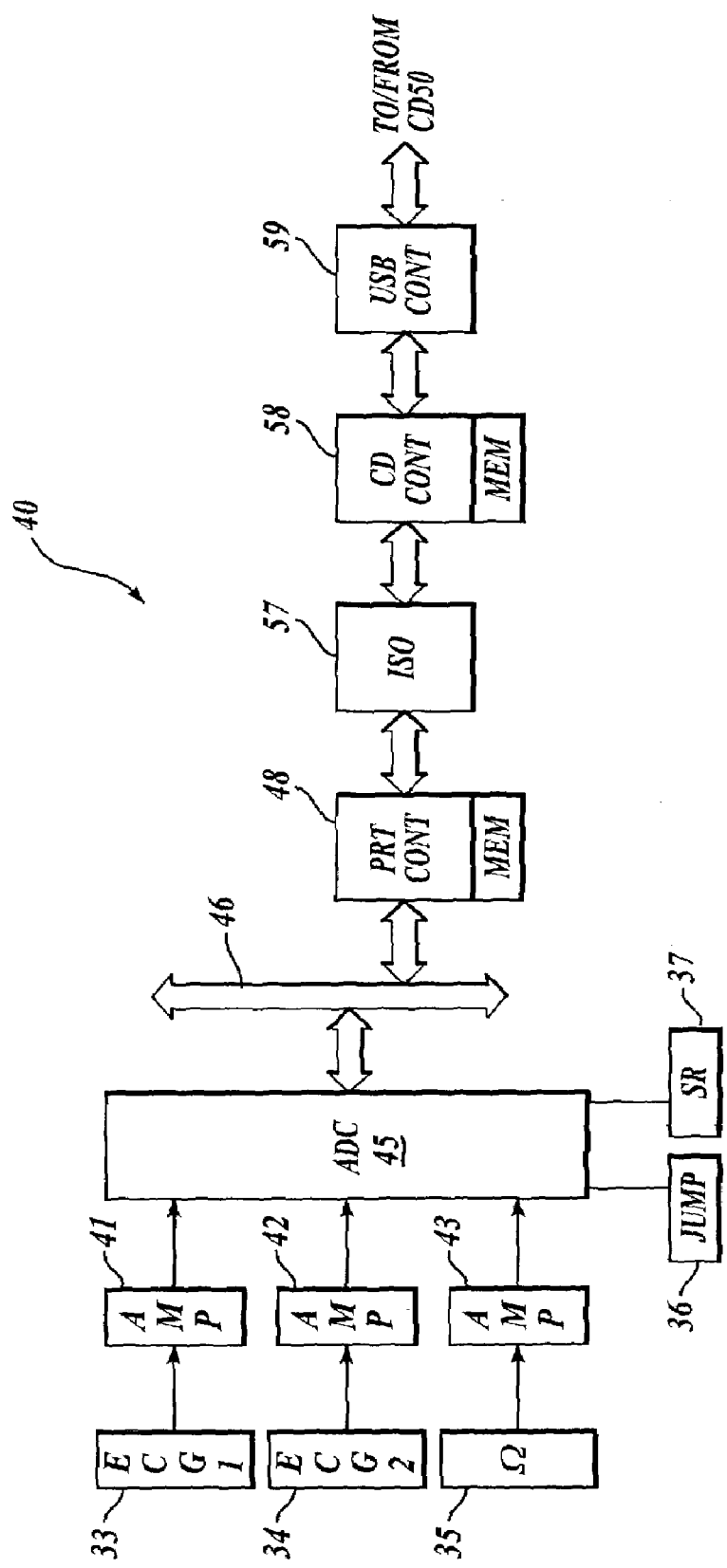
FIG. 5 shows a schematic diagram of an interface device useful in the system shown in FIG. 4.

Referring to FIG. 5, a schematic diagram of an interface device 40 useful in the practice of the present invention is shown. Interface device 40 preferably includes a plurality of sensor ports: ECG1 33 for heart rate variability sensors 21–24, ECG2 34 for additional Differential ECG sensors 25–27, omega port 35 for omega wave sensors 28–29, jump port 36 for jump sensor 30 and stimulus response port 37 for stimulus response sensor 31. Amplifiers 41–43 provide amplification of ECG and omega wave signals. Data from each of the ports is preferably digitized by ADC 45 and propagated onto bus 46.

Data flow on and off bus 46 is controlled in part by PRT-side microcontroller 48. A similar CD-side microcontroller 58 is also provided. These controllers 48, 58 are preferably separated by a galvanic isolator 57 which protects a person receiving a test from electric shock due to CD-side malfunction. Sensed data is selectively propagated from bus 46 to CD 50. A USB controller or the like 59 controls propagation of sensed data to CD 50 (over cable 44) and receipt of signals from CD 50 such as initialization and port selection requests.

Figure 6:
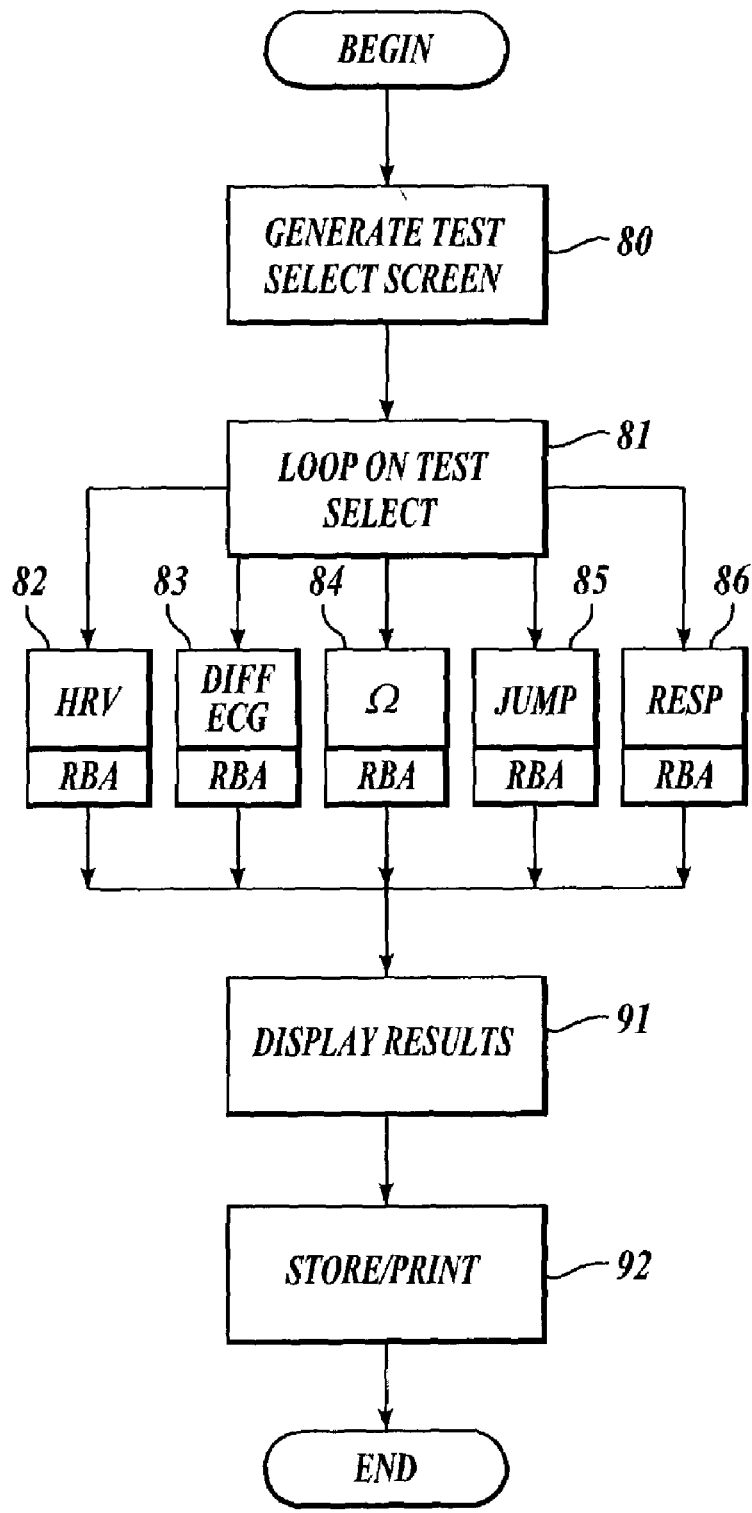
FIG. 6 shows a diagram that provides a general overview of testing procedures using the system shown in FIG. 4.

Referring to FIG. 6, a high level flow diagram of machine executable steps for performing a functional state assessment using system 10, such as heart rate variability analysis, is shown. In step 80, logic in CD 50 preferably generates a display on monitor 52 that permits a user to select the test or tests to be performed. Upon selection of a test, flow is routed to the code for executing the selected test (step 81). Blocks 82–86 represent logic for executing one or more of the following tests: Heart Rate Variability (selected in the practice of the present invention); Differential ECG; Omega Wave; Jump; and Stimulus Response.

The RBA block within blocks 82–86 represents the preferred rules-based analysis for determining textual conclusions of functional state. Step 91 represents code or logic for displaying test results (which may include calculated indices and textual conclusions) and step 92 represents print out or longer term storage of the test results.

Figure 7:
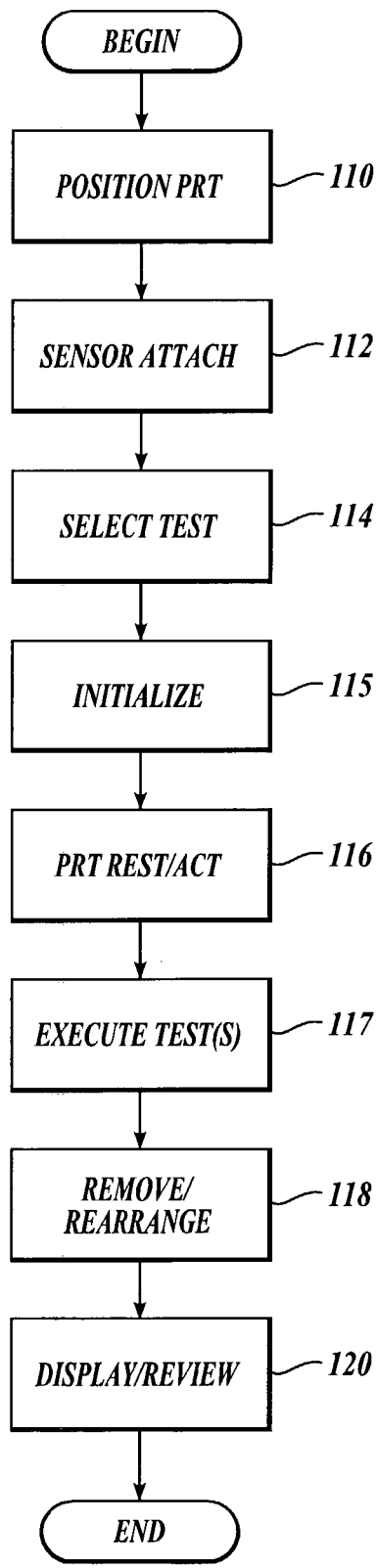
FIG. 7 shows a diagram that sets forth the steps, in a representative embodiment of the invention, for conducting a heart rate variability test using the system shown in FIG. 4.

Referring to FIG. 7, a diagram that illustrates the steps of conducting a heart rate variability test in accordance with the present invention is shown. In step 110, a person receiving a test (PRT) positions him or herself for sensor attachment. In step 112, the sensors are attached. In step 114, a user selects the desired heart rate variability test from CD 50. In step 115, ID 40 is initialized for appropriate data sensing and data propagation by CD 50. In step 116, the PRT is instructed to attain or maintain a state of rest. In step 117, the machine executable steps of the selected test(s) is/are carried out by CD 50. After test completion, the sensor electrodes are removed or rearranged (step 118) and the results are displayed for review (step 120). The results may be displayed on monitor 52 or printed via printer 60 or displayed by some other display mechanism. A description of machine executable steps of the heart rate variability test selected in step 114 of FIG. 7 is now presented. Processing cardiac signals as discussed below permits quantitative and qualitative analysis of the functional state of cardiac activity.

In general, a heart rate variability test conducted using system 10 records sensor data, constructs charts or "grams" (e.g., scatter-grams, histograms, frequency spectrum-grams) that display a representation of the sensed data, calculates indices from the "grams" and data, and performs rules based analysis of the indices values to generate textual conclusions of the functional state of cardiac activity.

Figure 8:
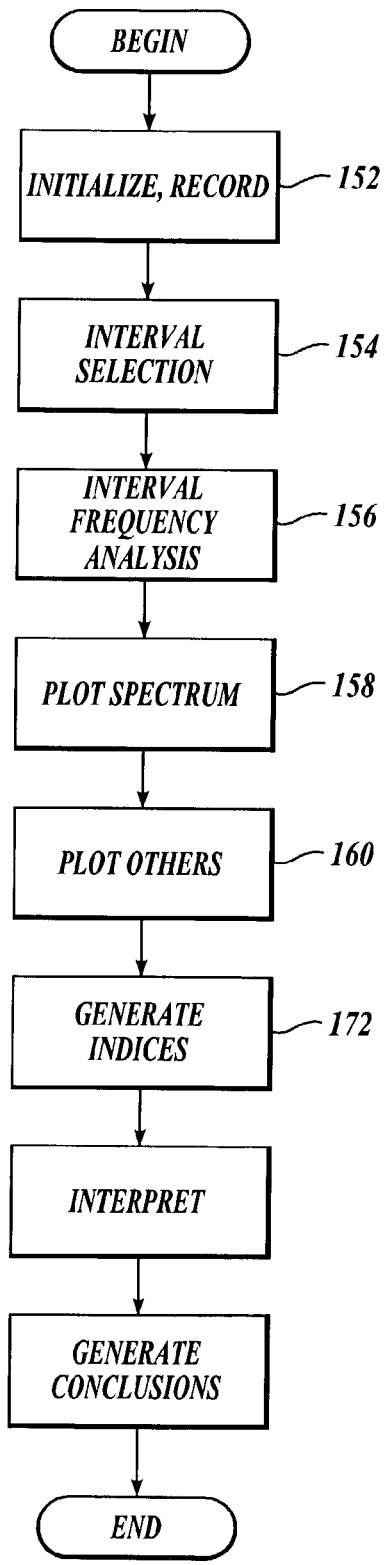
FIG. 8 shows a flow diagram of machine executable steps for a representative heart rate variability test using the system shown in FIG. 4.

A representative heart rate variability test is described with reference to FIG. 8, which illustrates a flow diagram of machine executing steps for a heart rate variability test in accordance with the present invention. The steps of FIG. 8 may be achieved with application software executing on the processor of CD 50 or via execution of machine executable steps using any applicable technology. A display of heart rate variability test results preferably includes a cardiogram, the above-mentioned charts/grams and textual conclusions of functional state.

In this representative heart rate variability test, four electrode sensors are preferably utilized and they are preferably placed one each on the wrists and ankles. One sensor electrode is a ground and the other three collect standard ECG data or the like. Alternative sensor placement may be utilized. The heart rate variability test is based on the registration of cardiac contractions of standard electrocardiogram (ECG) readings over the course of a fixed span of time. The test records the change of period length (in seconds) between each cardiac contraction which is the time between ECG spikes, which are designated with the letter R.

After initialization of ID 40, cardiac muscle electrical activity is recorded for a fixed time period, e.g., 128 seconds (step 152). A fixed number of consecutive heart beat intervals (RR intervals), e.g., 100, is selected and analyzed (step 154). The intervals are processed in this exemplary method using a fast Fourier transformation to achieve frequency spectrum analysis (step 156) and the density of interval frequencies is plotted in a frequency spectrum-gram (step 158). Frequency spectrum analysis is known in the art as described supra. The following frequency ranges are preferably plotted: high frequency=0.15 to 0.4 Hz; low frequency=0.04 to 0.15 Hz; and very low frequency=0.004 to 0.04 Hz. A histogram and a scattergram are also preferably generated and displayed (step 160).

In step 172, various indices for cardiovascular system performance are calculated based on frequency spectrum and other data and these include: Vagus (parasympathetic) Regulation (VR); Humoral Regulation (HR); Sympathetic Regulation (SR); Tension (Stress) Index; Share of aperiodic influences; Standard deviation; and Frequency of Cardiac Contractions (FCC). Calculation of these or related indices is known in the art. (See, e.g., Baevskiy, R. M., et al., Mathematical Analysis of Changes in Heart Rate Rhythm Under Stress, Moscow Science, 1984). These indices may be interpreted to generate textual conclusions about the functional state of cardiac activity.

In the practice of the present invention, heart rate variability data is analyzed to determine whether there is excessive sympathetic nervous system activity in the heart of a human being suffering from an autoimmune disease or fibromyalgia. The autonomic nervous system activity in the heart is a balance between sympathetic (stimulatory) and parasympathetic (inhibitory) nervous activity. Thus, by way of example, excessive sympathetic nervous system activity can occur in the following situations: a normal level of sympathetic nervous system activity and a lower than normal level of parasympathetic nervous system activity; a normal level of parasympathetic nervous system activity and a higher than normal level of sympathetic nervous system activity; and a lower than normal level of parasympathetic nervous system activity and a higher than normal level of sympathetic nervous system activity.

A normal level of sympathetic and/or parasympathetic nervous system activity can be determined, for example, by measuring sympathetic and/or parasympathetic nervous system activity in a population of healthy human beings, and using art-recognized statistical techniques to analyze the measured activity to yield a range of values for the normal level of activity of the sympathetic and/or parasympathetic nervous system(s). Thus, for example, the low and high frequency ranges of the Power Spectral Density of heart beat variation can be used as indicators of sympathetic and parasympathetic nervous system activity, respectively.

The OmegaWave Sport Technology System, described herein and in published United States patent application serial number U.S. 2002/0045835 A1, provides three values that can be used singly, or in combination, to determine whether sympathetic nervous system activity predominates over parasympathetic nervous system activity in the heart: activity of the vagus (parasympathetic) regulation mechanisms; activity of the sympathetic regulation mechanisms; and Tension index. Thus, the following are indications of sympathetic nervous system predominance: a value for the activity of the vagus (parasympathetic) regulation mechanisms that is lower than the normal range of values for activity of the vagus (parasympathetic) regulation mechanisms; a value for the activity of the sympathetic regulation mechanisms that is higher than the normal range of values for activity of the sympathetic regulation mechanisms; and a value for the Tension Index that is higher than the normal range of values for the Tension Index. System 10 provides the user with normal value ranges for activity of the vagus (parasympathetic) regulation mechanisms, activity of the sympathetic regulation mechanisms; and tension index.

The foregoing indices may be combined to facilitate a more accurate determination of whether sympathetic nervous system activity predominates over parasympathetic nervous system activity in the heart. For example, if the value for the activity of the sympathetic regulation mechanisms is slightly higher than the normal range of values for activity of the sympathetic regulation mechanisms, then a medical practitioner may also determine whether the value for the activity of the vagus (parasympathetic) regulation mechanisms is lower than the normal range of values for activity of the vagus (parasympathetic) regulation mechanisms. The coexistence of even a slightly higher than normal sympathetic nervous system value with even a slightly lower than normal parasympathetic nervous system value strengthens the conclusion that sympathetic nervous system activity predominates over parasympathetic nervous system activity in the heart.

In some embodiments of the methods of the present invention, the heart rate variability of a human being suffering from an autoimmune disease, and/or fibromyalgia, is measured and analyzed over a period of less than one hour, such as over a period of less than half an hour, such as over a period of less than fifteen minutes, such as over a period of less than five minutes. In some embodiments of the methods of the present invention, the heart rate variability of a human being suffering from an autoimmune disease, and/or fibromyalgia, is measured and analyzed over a period of from one minute to three minutes, such as over a period of two minutes. The ability to measure and analyze the heart rate variability of a human being over only a few minutes facilitates rapid determination, in a clinical setting, of whether to provide an inhibitor of sympathetic nervous system activity to a human being suffering from an autoimmune disease and/or fibromyalgia.

In the practice of the present invention, if it is determined that excessive sympathetic nervous system activity exists in the heart of the subject human being, then an inhibitor of sympathetic nervous system activity is provided to the human being. Representative examples of inhibitors of sympathetic nervous system activity include magnesium supplements; Valerian root; Parkinson's disease medications (including carbolevodopa, pergolide (Permax), pramipexole (Mirapex), ropinirole (Requip), and Sumanerol); antiepileptics (including Depakote, pregabalin, gabapentin (Neurontin)); benzodiazepines (including lorazepam and clonazepam); antidepressants (including tricyclics such as amitriptyline and nortriptyline, trazodone, (Remeron), nefazodone (Serzone) and brupropion (Wellbutrin SR)); anxiotytics (including buspirone, alprazolam (Xanax) and serotonin reuptake inhibitors, including fluoxetine (Prozac), paroxetine (Paxil), sertraline (Zoloft), citalopram (Celexa), and escitalopram (Lexapro)); mixed norepinepherine/serotonin reuptake inhibitors (including milnacipram, venlafaxine (Effexor), tizanidine (Zanaflex), carisoprodol (SOMA), and cyclobenzaprine (Flexeril)); alpha 2 central agonists (including clonidine and derivatives). Typical doses for these compounds are set forth, for example, in the United States Pharmacopeia.

In the practice of the present invention, an inhibitor of sympathetic nervous system activity is provided to a human being suffering from an autoimmune disease, and/or fibromyalgia, if there is excessive sympathetic nervous system activity in the heart of the human being. In this context, the term "providing" encompasses directly providing the human being with an inhibitor of sympathetic nervous system activity (e.g., a physician gives a patient, who is suffering from an autoimmune disease and who has excessive sympathetic nervous system activity, one or more pharmacologically active compounds that is/are effective to inhibit sympathetic nervous system activity). Typically, the one or more pharmacologically active compounds is/are provided in a form (e.g., tablets) that the patient can administer to himself/herself according to instructions provided by a health care provider.

The term "providing" also encompasses embodiments of the invention in which the step of providing is satisfied by a health care provider giving a patient a prescription for an inhibitor of sympathetic nervous system activity. The prescription may be given directly to the patient, or the prescription may be given to a pharmacist, or pharmacist's assistant, or other provider of medications, and the patient then collects the filled prescription. Thus, in these embodiments, a pharmacist, or pharmacist's assistant, physically gives the inhibitor of sympathetic nervous system activity to the patient. The patient may then administer the inhibitor of sympathetic nervous system activity to himself/herself in accordance with the instructions provided by a physician, pharmacist or other health care provider.

The following examples merely illustrate the best mode now contemplated for practicing the invention, but should not be construed to limit the invention.

EXAMPLE 1

This Example shows the use of system 10 to demonstrate that rheumatoid arthritis patients who did not respond to the arthritis medication etanercept alone, but required a combination of arthritis medications, suffered from excessive sympathetic nervous system activity.

Thirty-one patients with rheumatoid arthritis (RA) were evaluated. All patients had taken etanercept (Enbrel®, Amgen Corp.) for at least six months to allow patients to reduce or eliminate other RA medications if possible. To consider why some patients responded to etanercept alone while others required etanercept combined with other medications, demographic variables were compared, including gender, age, RA duration, presence of RA nodules, vasculitis, rheumatoid factor, anti-nuclear antibody, erthrocyte sedimentation rate, C-reactive protein, hematocrit, weight and duration of etanercept use. Disease activity was assessed by examination and the Multi-Dimensional Health Assessment Questionnaire (MDHAQ). A correlation was not observed between any of the foregoing variables and a requirement for etanercept combined with other medications.

The patients were also evaluated using system 10 described herein, and the Beck Anxiety Index, to measure autonomic dysfunction. The Beck Anxiety Index is a validated tool to measure anxiety. Higher scores correlate with increased anxiety, and a sub-score measures autonomic activity, such as sweating, palpitations and dizziness. The existence of a statistically significant correlation between the presence of excessive sympathetic nervous system activity and the requirement for etanercept alone, or a combination of etanercept with other RA medications, was determined using the Pearson correlation test. A perfect Pearson correlation would be 1.000 with p approaching zero with the 2-tailed test.

As shown in Table 1, three measures of autonomic function, measured using system 10, predicted which patients would require etanercept alone versus more toxic and expensive combination medications to effectively treat RA: the Vagus parasympathetic (Pearson correlation value of −0.409 at $p<0.05$), the sympathetic (Pearson correlation value of 0.410 at $p<0.05$) and the Tension Index (Pearson correlation value of 0.506 at $p<0.05$).

As shown in Table 1, increased sympathetic nervous system activity, measured by BAI total score, BAI autonomic sub-score, HRV sympathetic and tension index measurements, correlated strongly with a requirement for a combination of etanercept with other RA medications to effectively treat RA. Those patients responding to etanercept alone had much lower measures of sympathetic nervous system activity.

The Vagus score inversely correlated with a requirement for a combination of RA medications as expected, since it measures the opposition of sympathetic nervous system activity.

TABLE 1

|     |              | Mono  | Comb  | Pearson |
| --- | ------------ | ----- | ----- | ------- |
| BAI | Total        | 3.68  | 12.50 | .550**  |
|     | Autonomic    | 1.16  | 3.17  | .423*   |
| HVA | Vagus        | 0.17  | 0.12  | −.409*  |
|     | Sympathetic  | 51    | 65    | .410*   |
|     | Tension Index| 217.8 | 490.9 | .506*   |
|     | Total Power  | 516.1 | 351.8 | (NS)    |

*$p < .05$
**$p < .001$
(NS) no significant correlation

Traditional risk factors for disease activity and medication requirements were completely unrevealing. Only measures of autonomic function, including the use of system 10 to measure heart rate variability, and the Beck Anxiety Index, could assist the physician to formulate a more effective approach to controlling RA.

EXAMPLE 2

This Example describes the use of system 10 to demonstrate that excessive sympathetic nervous system activity is associated with active multiple sclerosis.

Heart rate variability in five patients suffering from Multiple Sclerosis (MS) was assessed using system 10. Two patients had experienced from one to three MS flares over the past year; three were in MS remission. As shown in Table 2 below, subjects without MS activity had significantly higher vagus and lower sympathetic and tension scores compared to those with MS activity. Values in brackets represent the normal range for each type of measurement.

TABLE 2

| Patient | MS activity | vagus (.16–.41) | sympathetic (15–55) | tension (15–180) | total power |
| --- | --- | --- | --- | --- | --- |
| G.D. | remission | .26 | 37 | 59 | 3402 |
| J.S. | remission | .17 | 51 | 220 | 236 |
| L.L | flares | .09 | 52 | 302 | 66 |
| D.M. | flares | .09 | 55 | 488 | 119 |
| M.Z. | flares | .09 | 53 | 412 | 91 |

EXAMPLE 3

This example shows that medication to reduce excessive sympathetic nervous system activity in a patient suffering from severe, previously untreatable, psoriatic arthropathy caused a reduction in the severity of the disease.

Over a period of fifteen years, the patient suffered chronic joint flares, and exceptional synovial thickening that was resistant to all know treatments, including Etanercept. Pramipexole was then administered to the patient and increased to a dosage of 2.0 mg per day at bedtime. The patient's restlessness and insomnia improved and etanercept became more effective over six weeks. The following heart rate variability measurements were made in the patient using system 10: vagus, 0.16; sympathetic, 54; tension, 220; total power, 283.

As the dosage of pramipexole was increased over a period of 4 weeks to 4.5 mg per day at bedtime, joint swelling and pain improved significantly, and excessive sympathetic nervous system activity decreased: vagus, 0.19; sympathetic, 43; tension, 145 (now normal); total power 319. The improvements in the patient's condition have persisted for two years.

EXAMPLE 4

This example shows that the level of excess sympathetic nervous system activity in the hearts of human patients suffering from systemic lupus erythematosus correlated closely with the level of disease activity, and that the level of excess sympathetic nervous system activity in the hearts of seven human patients suffering from systemic lupus erythematosus correlated closely with the amount of steroids required to treat the disease.

Pramipexole was administered to a patient suffering from systemic lupus erythematosus, in addition to traditional steroid therapy. The patient's alopecia, pleurisy, arthritis, fatigue and fever all improved as excessive sympathetic nervous system activity decreased. The patient's heart rate variability was monitored using system 10. As shown in Table 3, the level of excess sympathetic nervous system activity in the patient's heart correlated closely with the level of disease activity over four months.

TABLE 3

| Date | Disease activity | vagus | sympathetic | tension | total power |
|---|---|---|---|---|---|
| Oct. 10, 2001 | Severe activity | .05 | 93 | 1444 | 29 |
| Nov. 14, 2001 | no improvement | .05 | 93 | 1278 | 24 |
| Dec. 11, 2001 | mild activity | .10 | 61 | 374 | 102 |
| Feb. 5, 2002 | moderate flare | .09 | 87 | 569 | 128 |

Additionally, as shown in Table 4, the level of excess sympathetic nervous system activity in the hearts of seven systemic lupus erythematosus patients correlated closely with the amount of steroids required to treat systemic lupus erythematosus.

TABLE 4

| Patient | Prednisone dose | vagus | sympathetic | tension | total power |
|---|---|---|---|---|---|
| N.H. | 10 mg | .07 | 59 | 468 | 46 |
| D.M | 5 mg | .12 | 73 | 399 | 152 |
| L.P. | 2 mg | .13 | 81 | 372 | 85 |
| O.C. | none | .11 | 53 | 294 | 139 |
| C.N. | none | .16 | 48 | 150 | 615 |
| L.R. | none | .17 | 48 | 138 | 406 |
| L.P | none | .19 | 59 | 157 | 1824 |
| Pearson Correlation With Prednisone dose | | −.799* | .328# | .841* | −.451# |

(*$p < .05$ #no significant correlation)

EXAMPLE 5

This example shows the symptoms of a female patient suffering from autoimmune hemolytic anemia improved in response to administration of pramipexole which reduced excessive sympathetic nervous system activity, and relapsed when the patient stopped taking the pramipexole.

Patient S. H. suffered from autoimmune hemolytic anemia. The patient had leukopenia (reduced white blood cell (WBC) count; 2,300 WBC). Steroids were recommended, but the patient refused. The patient's heart rate variability was monitored using system 10: vagus, 0.17; sympathetic, 52; tension, 199; total power, 201. Although autonomic function was only mildly abnormal (sympathetic nervous system activity was elevated), the patient had refused steroids and so had few other treatment options. Therefore, pramipexole was prescribed for administration at night to address sympathetic overactivity. The patient's symptoms improved, and her WBC count began to increase (2400). These changes correlated with a reduction in excessive sympathetic nervous system activity: vagus, 0.22; sympathetic, 45; tension, 147; total power, 294.

The patient discontinued pramipexole against medical advice. WBC decreased to 2100 as excessive sympathetic nervous system activity increased: vagus, 0.20; sympathetic, 70; tension, 236; total power, 280.

EXAMPLE 6

This Example shows that the level of disease activity in three patients suffering from Behcet's disease correlated with the level of excessive sympathetic nervous system activity.

Three patients were assessed by measuring heart rate variability using system 10. The level of disease activity correlated with the level of excessive sympathetic nervous system activity as shown in Table 5.

TABLE 5

| Patient | Disease activity | vagus | sympathetic | tension | total power |
|---|---|---|---|---|---|
| M.L | Active | .12 | 69 | 292 | 97 |
| C.G. | Inactive | .21 | 35 | 103 | 465 |
| A.B. | Inactive | .25 | 38 | 80 | 713 |

EXAMPLE 7

This example shows successful treatment of previously untreatable ankylosing spondylitis by administering traditional therapeutic agents in combination with pramipexole which reduces excessive sympathetic nervous system activity.

A male patient, L. D., suffered from Ankylosing Spondylitis and required narcotic analgesia, excessive prednisone (40 mg per day) that led to avascular necrosis of both hips and hip replacement. Etanercept and methotrexate failed to control his disease. The patient's heart rate variability was measured using system 10 and yielded the following values: vagus, 0.06; sympathetic, 81; tension, 998; total power, 68; thereby revealing significant excessive sympathetic nervous system activity, and parasympathetic nervous system underactivity. Consequently, the patient was provided with the following treatment: etanercept, prednisone (5 mg per day) and pramipexole (4.5 mg per day at bedtime). So far the disease has been successfully controlled with this treatment for a period of two years.

EXAMPLE 8

This example shows that the presence of excessive sympathetic nervous system activity, in human patients suffering from fibromyalgia (FM), positively correlates with the level of pain experienced by the fibromyalgia sufferers.

System 10 was used to measure heart rate variability in fifty two consecutive patients with chronic FM (41 females, 11 males, mean weight 184.5 lbs, mean age 48.8, FM duration 8.9 years, mean FM medications used was 6.5) at a private, referral-based rheumatology clinic. Co-morbidities included: degenerative spine pain 58%, anxiety 21%, depression 21%, bipolar 10%. Medication use: benzodiazepines 33%, PM antidepressant 39%, narcotic 35%, dopamine agonist 25%, SSRI 23%, antipsychotic 12%, NSAID 33%, antiepileptic 21%.

Pain score (on a scale of 0–54) was the sum of 18 classic tender points, each scored by severity (0=painless, ½=minimal, 1=4 kg, 2=severe, 3=exquisite.) Mean Pain Score was 18.0 despite current treatment. Table 6 shows the Pearson correlation values for correlation between various measures of disease state (BAI and its subcomponents, MDHAQ and its subcomponents, and the vagus, sympathetic and tension index values measured using system 10) and tender point pain score. The larger the Pearson correlation value, the stronger is the correlation.

TABLE 6

| BAI | | MDHAQ | | HVA | |
|---|---|---|---|---|---|
| TOTAL | 0.495** | Function | 0.626** | Vagus | −0.172# |
| Panic | 0.493** | Psych | 0.467** | Sympathetic | 0.132* |
| Subjective | 0.350* | Pain | 0.570** | Tension Index | 0.376** |
| Neuro | 0.388* | Stiffness | 0.531** | Total Power | −0.243# |
| Autonomic | 0.252# | Fatigue | 0.425** | | |
| | | Global | 0.684** | | |

*$p < 0.05$;
**$p < 0.01$;
$p > 0.05$.

While the preferred embodiment of the invention has been illustrated and described, it will be appreciated that various changes can be made therein without departing from the spirit and scope of the invention.

The invention claimed is:

1. A method to determine whether to provide an inhibitor of sympathetic nervous system activity to a human being suffering from an autoimmune disease or fibromyalgia, wherein the method comprises the steps of:
   (a) measuring the heart rate variability of a human being suffering from an autoimmune disease or fibromyalgia, to yield heart rate variability data;
   (b) analyzing the heart rate variability data to determine whether the heart rate variability is lower than a normal value and whether sympathetic nervous system activity in the heart of the human being exceeds a predetermined value; and
   (c) providing an inhibitor of sympathetic nervous system activity to the human being if sympathetic nervous system activity exceeds said predetermined value in the heart of the human being.

2. The method of claim 1 wherein the autoimmune disease is selected from the group consisting of rheumatoid arthritis, psoriatic arthritis, spondyloarthropathy, palindromic rheumatism, systemic lupus erythematosus, vasculitis with systemic lupus erythematosus, multiple sclerosis, Hashimoto's thyroiditis, chronic pseudogout, hepatitis C arthritis, mixed connective tissue disease, dermatomyositis, polymyositis, scleroderma, Sjogren's syndrome, cryoglobulinemia, Crohn's disease, ulcerative colitis, autoimmune hepatitis, sclerosing cholangitis, primary biliary cirrhosis, autoimmune pneumonitis, autoimmune cerebritis, thyroiditis, graft versus host disease, Myasthenia gravis, pemphigus vulgaris, temporal arteritis, polymyalgia rheumatica, autoimmune hemolytic anemia, idiopathic thrombocytopenic purpura, thrombotic thrombocytopenic purpura, hemolytic uremic syndrome, Sweet's syndrome, polyarteritis nodosa, microscopic polyarteritis nodosa, amyloidosis, sarcoidosis and familial Mediterranean fever.

3. The method of claim 1 wherein heart rate variability is measured by measuring the temporal variation between the occurrence of the same electrocardiogram feature on a multiplicity of successive heart beats.

4. The method of claim 3 wherein the electrocardiogram feature is selected from the group consisting of a P wave, a Q feature, an R peak, an S feature and a T wave.

5. The method of claim 3 wherein heart rate variability is measured by measuring the temporal variation between R peaks on a multiplicity of successive heart beats.

6. The method of claim 1 wherein heart rate variability is analyzed using Fourier transformation analysis of the heart rate variability data.

7. The method of claim 1 wherein it is determined that excessive sympathetic nervous system activity exists in the heart of the human being by observing the presence of a normal level of sympathetic nervous system activity and a lower than normal level of parasympathetic nervous system activity.

8. The method of claim 1 wherein it is determined that excessive sympathetic nervous system activity exists in the heart of the human being by observing the presence of a normal level of parasympathetic nervous system activity and a higher than normal level of sympathetic nervous system activity.

9. The method of claim 1 wherein it is determined that excessive sympathetic nervous system activity exists in the heart of the human being by observing the presence of a lower than normal level of parasympathetic nervous system activity and a higher than normal level of sympathetic nervous system activity.

10. The method of claim 1 wherein steps (a) and (b) together occur within a period of less than one hour.

11. The method of claim 10 wherein steps (a) and (b) together occur within a period of less than half an hour.

12. The method of claim 10 wherein steps (a) and (b) together occur within a period of less than five minutes.

* * * * *

UNITED STATES PATENT AND TRADEMARK OFFICE
CERTIFICATE OF CORRECTION

PATENT NO. : 7,146,205 B2  Page 1 of 1
APPLICATION NO. : 10/441922
DATED : December 5, 2006
INVENTOR(S) : A.J. Holman It is certified that error appears in the above-identified patent and that said Letters Patent is hereby corrected as shown below:

| COLUMN | LINE | ERROR |
|---|---|---|
| Title Page, item (54) Pg. 1, col. 1 | Title | "FIBRYOMYALGIA" should read --FIBROMYALGIA-- |
| Title Page, item (56) col. 1 | Refs. Cited (Other Publs., Item 8) | "Measurements of Variability" should read --Measurements of Heart Rate Variability-- |
| Col. 1 | 6 | "FIBRYOMYALGIA" should read --FIBROMYALGIA-- |
| 10 | 36 | before "alpha 2" insert --and-- |

Signed and Sealed this

Third Day of April, 2007

JON W. DUDAS
*Director of the United States Patent and Trademark Office*